United States Patent [19]

Barnes

[11] Patent Number: 5,156,624
[45] Date of Patent: Oct. 20, 1992

[54] HEAD ADAPTOR FOR HIP PROSTHESIS

[75] Inventor: Milton F. Barnes, Warsaw, Ind.

[73] Assignee: Zimmer, Inc., Warsaw, Ind.

[21] Appl. No.: 755,969

[22] Filed: Sep. 6, 1991

[51] Int. Cl.⁵ ................................. A61F 2/32
[52] U.S. Cl. .......................... 623/22; 623/18
[58] Field of Search ..................... 623/22, 18, 66

[56] References Cited

U.S. PATENT DOCUMENTS

| | | |
|---|---|---|
| 4,015,257 | 5/1977 | Crowninshield et al. ........... 623/22 |
| 4,676,797 | 6/1987 | Anapliotis et al. .................. 623/18 |
| 4,750,905 | 6/1988 | Koeneman et al. .................. 623/16 |
| 4,921,500 | 5/1990 | Averill et al. ........................ 623/22 |
| 4,957,510 | 9/1990 | Cremascoli ........................... 623/23 |
| 4,963,155 | 10/1990 | Lazzeri et al. ...................... 623/23 |
| 4,995,883 | 2/1991 | Demane et al. ...................... 623/18 |
| 5,002,581 | 3/1991 | Paxson et al. ....................... 623/18 |

FOREIGN PATENT DOCUMENTS

| | | |
|---|---|---|
| 0202141A2 | 11/1986 | European Pat. Off. . |
| 0202141 | 11/1986 | European Pat. Off. . |
| 2618763 | 11/1976 | Fed. Rep. of Germany ........ 623/18 |

OTHER PUBLICATIONS

Orthopaedic Device Corporation brochure—"A New Generation Proportional Hemi-Prosthesis"—No date available.
Richards catalog p. 51—"Trunnion Sleeve"—1987.
Zimmer, Inc. brochure—"The Total System"—Lit. No. 85-037-9026-0326—1984.
Allo Pro brochure—"Rotation-type Hip Joint Prosthesis, Weber System"—1984.

Primary Examiner—David Isabella
Assistant Examiner—Gina M. Gualtieri
Attorney, Agent, or Firm—Margaret L. Geringer

[57] ABSTRACT

A set of hip prosthesis components including a plurality of head components and an adaptor component for use in assembling together one of the head components and a femoral stem component. The first head component is an endo head component having a first bore of a first shape or length. The second head component includes a second bore that is of a second shape or length different from the first shape or length. The adaptor includes an axially extending protruding portion wherein the first shape or length of the first bore is sufficient for the bore to accept and frictionally retain therein the protruding portion. The second shape or length of the second bore is insufficient or inappropriate for the second bore to frictionally retain therein the protruding portion.

7 Claims, 2 Drawing Sheets

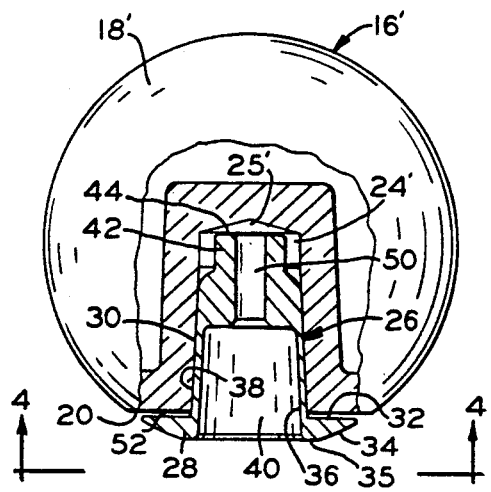
FIG_3
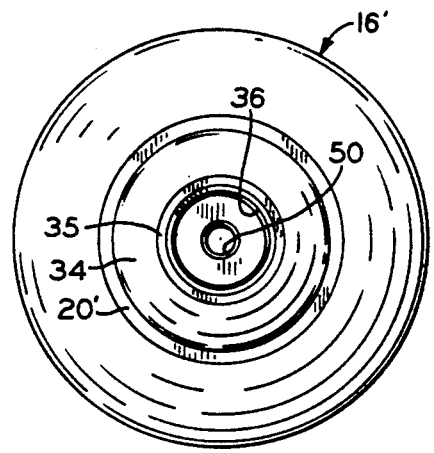
FIG_4
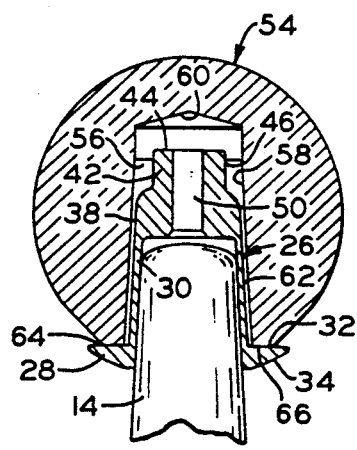
FIG_5
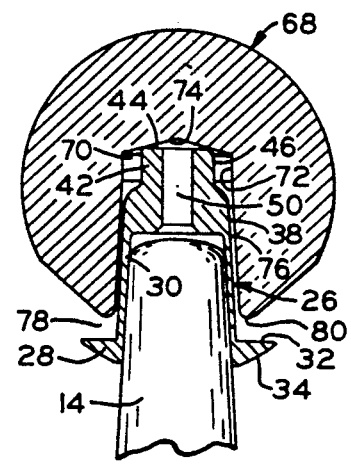
FIG_6
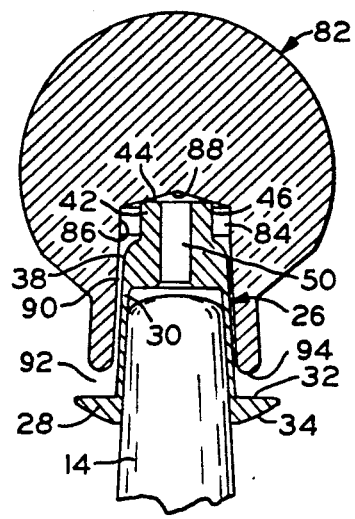
FIG_7

HEAD ADAPTOR FOR HIP PROSTHESIS

BACKGROUND OF THE INVENTION

The present invention relates generally to prosthetic hip implants and, more particularly, to an adaptor for attaching a spherical head component to a femoral stem component.

Conventional prosthetic hip joints generally include a femoral component having a spherical head member affixed to the femur by means of a femoral stem secured within the femur. In the case of total hip replacement, a so-called standard femoral head is used and is adapted to be received within an acetabular cup that is inserted into the acetabulum of the hip socket. In the case of a hip replacement that does not require a separate acetabular cup, an endoprosthesis (endo) head is utilized and mates directly with the acetabulum. Since endo heads mate directly with the acetabulum, they have a larger spherical diameter than standard femoral heads used with prosthetic acetabular cups.

Standard femoral heads are produced in a variety of neck lengths (i.e. "short", "medium", and "long") to provide optimal prosthesis-to-patient fit, where "short", "medium", and "long" relate to the center of rotation of the head relative to the stem taper. In contrast, endo heads are typically produced having the same location for the center of rotation with respect to the hip stem taper, i.e., the same neck length, and this location is independent of the spherical size of the head. Accordingly, an interpositional plug or head adaptor is required in those cases in which it is necessary to increase the neck length for such an endo head.

When performing hip replacement surgical procedures, the physician has available many different varieties of femoral head components and stem components in a variety of different sizes. Essentially, the physician must select the size necessary to form a joint that matches the physiology of the patient's hip. Once a particular femoral stem component is selected, the proper head with the appropriate neck length must be selected. In the case of total hip replacements, the physician chooses the standard femoral head component having the desired neck length.

Problems could arise when a head adaptor is available to provide an extended neck length for an endo head because the endo head adaptor could be inadvertently assembled to a standard size head. This would be a particular problem if the endo head adaptor was assembled to a standard head which already had a built-in extended neck length and therefore too long of a neck would be provided. In addition, the endo head adaptor may not be suitably seated within and sufficiently supported by the smaller standard head, thereby causing excessive pressures to be exerted on the thin wall of the endo head adaptor. Eventually, the adaptor will wear prematurely and must be replaced.

SUMMARY OF THE INVENTION

The present invention overcomes the above problems and disadvantages by providing an adaptor for assembling a spherical femoral head component to the neck of a stem component for a hip prosthesis, wherein the adaptor is configured so that it is properly seated and frictionally retained within the bore of a first, proper size head component, but the adaptor will not be frictionally retained and seated within the bore of a second, improper size head component, wherein the bore of the second head component is of a different shape or different length than the bore of the first head component.

Generally, the present invention provides a set of hip prosthesis components having a plurality of head components and an adaptor for use in assembling together one of the head components and a femoral stem component. The adaptor includes an axially extending protruding portion that is configured for engagement with the bore of a selected head component. A first head component includes a first bore having a shape or length that is sufficient for the first bore to properly seat and frictionally retain therein the protruding portion. A second head component includes a second bore having a shape or length that is insufficient or inappropriate for the second bore to properly seat and retain the protruding portion.

More particularly, the present invention provides, in one form thereof, an endo spherical head component, a standard femoral head component, and an adaptor having a protruding portion including a tapered outer surface that is frictionally engaged and retained by the inner seating surface of the bore of the endo head component. The bore depth of the standard femoral head is smaller than the bore depth of the endo head and is thus insufficient to seat and retain the protruding portion of the adaptor, thereby alerting the physician that the adaptor cannot be used with the standard head.

An advantage of the head adaptor of the present invention is that the adaptor is retained only in those bores in which it is properly seated.

Another advantage of the adaptor of the present invention is that the adaptor includes a rim portion that provides visual confirmation as to whether the adaptor is properly seated within a head.

An advantage of the head adaptor of the present invention is that the adaptor cannot be used with itself, thereby limiting its use to one adaptor for an endo head. A surgeon cannot use plural adaptors on one endo head. This is prevented or limited by the depth of the recess in relation to the overall length of the adaptor.

The present invention, in one form thereof, provides a set of hip prosthesis components including a plurality of head components and an adaptor component for use in assembling together one of the head components and a femoral stem component. One of the head components is selected for engagement with the adaptor component. Each of the head components includes a bore, and the adaptor component includes an axially extending protruding portion that is configured for engagement with the bore of a selected head. The plurality of head components includes a first head component having a first bore that is of a first shape or length, and a second head component including a second bore that is of a second shape or length. The adaptor is configured to securely seat within the first head component wherein the first shape or length of the first bore is sufficient for the first bore to accept and frictionally retain therein the protruding portion. The second shape or length of the second bore is insufficient or inappropriate for the second bore to frictionally retain therein the adaptor with its protruding portion.

The present invention, in one form thereof, provides a method of assembling the prosthesis. The first head component is selected from the set for engagement with the adaptor component. Next, the axially extending portion of the adaptor component is inserted into the first bore in the first head component, wherein the shape or length of the first bore is sufficient for the first bore to accept and frictionally retain therein the protruding portion. The shape or length of the second bore in the second head component is insufficient or inappropriate for the second bore to frictionally retain therein the protruding portion. A femoral stem component is attached to the adaptor component.

BRIEF DESCRIPTION OF THE DRAWINGS

FIG. 3 is an assembled sectional view of an endo head of a different size and the adaptor of FIG. 1.

FIG. 4 is an end view of the assembly of FIG. 3, taken along line 4—4 in FIG. 3.

FIG. 5 is a sectional view of a hip prosthesis assembly having a standard head with a short neck length, wherein the adaptor according to the present invention is shown inserted into the bore of the head and improperly seated therein.

FIG. 6 is a view similar to FIG. 5, except that a standard head having a medium neck length is depicted.

FIG. 7 is a view similar to FIG. 5, except that a standard head having a long neck length is depicted.

DESCRIPTION OF THE PREFERRED EMBODIMENT

Figure 1:
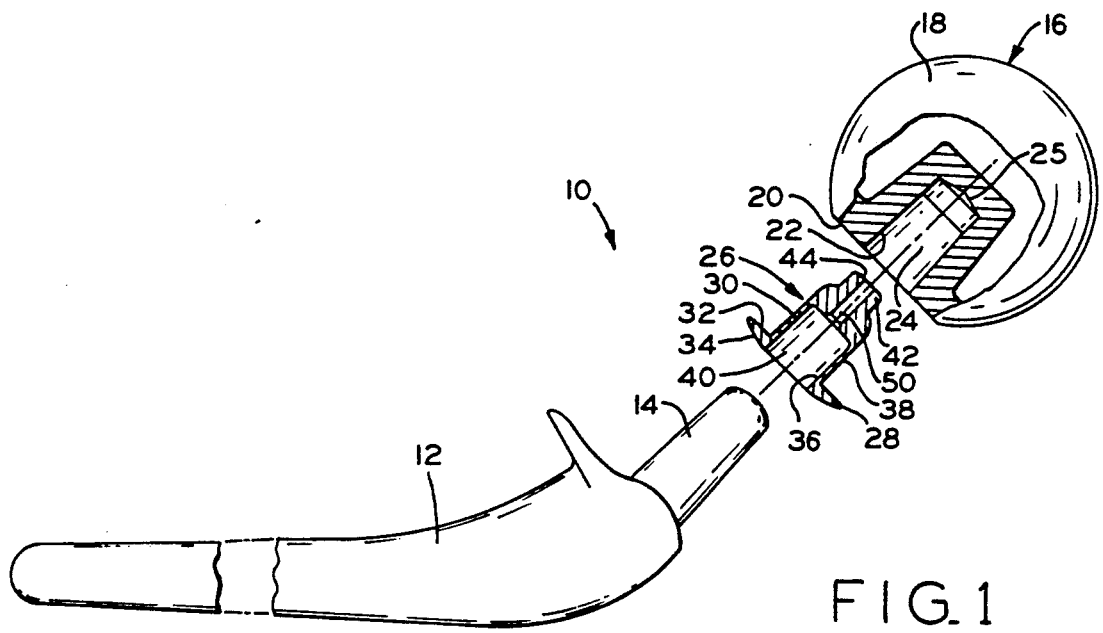
FIG. 1 is an exploded elevational view in partial crosssection of the hip prosthesis components according to the present invention.

In an exemplary embodiment of the invention as shown in the drawings, and in particular by reference to Fig. 1, a hip prosthesis 10 is shown including a stem component 12 having a conventional tapered neck 14, which is preferably a Morse-type taper. Stem component 12, which is designed to be received within a femur, may be made of any suitable biocompatible material, such as a titanium or cobalt-chrome alloy. Neck 14 is secured to a spherical head component by an attachment mechanism to be described hereinafter. As shown in FIG. 1, the spherical head component is an endoprosthesis (endo) head 16, which is directly insertable into the acetabulum of a hip socket.

Figure 2:
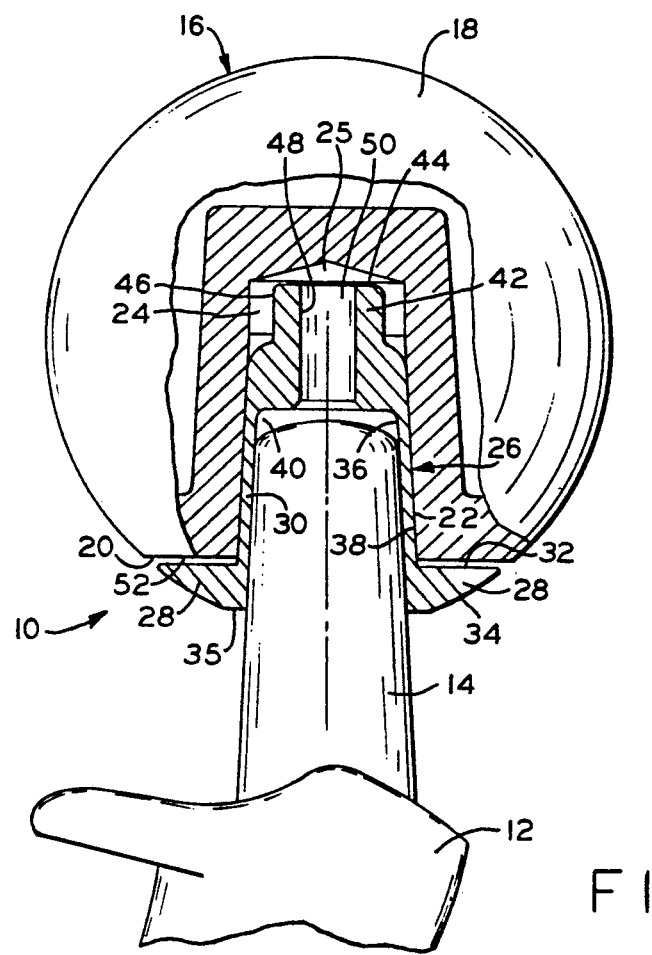
FIG. 2 is an enlarged fragmentary assembled view in partial cross-section of the hip prosthesis shown in FIG. 1.

The endo head 16 depicted in FIGS. 1 and 2 may be of any available diameter. For example, endo heads that are
commercially available from Zimmer, Inc., of Warsaw, Indiana, vary in head diameter from 38 mm. to 63 mm. in one millimeter increments to optimize prosthesis-to-patient fit. Referring again to FIG. 1, endo head 16, which may be made of any suitable biocompatible material, such as a cobalt-chrome alloy, includes a spherical surface 18 and a generally flat surface 20, wherein flat surface 20 includes a recessed inner seating surface 22 therein to define a tapered cylindrical recess or bore 24 for receiving neck 14 of stem component 12. Seating surface 22 is configured with a Morse-type taper to mate with neck 14 and is designed with a straight cylindrical portion and a conventional "tent-shape" tapered inner end 25.

In accordance with the present invention, an attachment mechanism or adaptor 26 is provided for assembling together neck 14 of stem 12 and head 16. The adaptor provides about a 7 mm increase in neck length. The adaptor is utilized to increase the neck length from a "medium" length to a "long" length. It is noted that there is no "short" length associated with the Zimmer endo heads described above. As shown in FIG. 1, adaptor 26, which may be made of any suitable biocompatible material, such as a titanium alloy, includes a generally annular rim portion 28, which increases rigidity of adaptor 26, and a generally cylindrical protruding portion 30. Rim portion 28 includes a flat inner face 32 and an opposite outer face comprising a radially outwardly curved face portion 34 and a radially inwardly flat face portion 35. Protruding portion 30 includes identically tapered inner 36 and outer 38 surfaces. Inner surface 36 defines a tapered socket 40 having the same taper as surface 22 for securely receiving and seating neck 14 therein. Adaptor 26 further includes a cylindrical reduced diameter portion 42 at the inner axial end of protruding portion 30 to form a raised boss. As best shown in FIG. 2, reduced diameter portion 42 includes a generally flat top surface 44, a cylindrical outer surface 46, and a cylindrical inner surface 48, which defines a cylindrical bore 50 that is concentric with socket 40. It is noted that the lower portion of cylindrical bore 50 extends downwardly from reduced diameter portion 42 and into cylindrical protruding portion 30 to provide an axially extending opening through adaptor 26.

According to the present invention, adaptor 26 is designed to securely and properly seat within only certain ones of a plurality of femoral head components, wherein other heads include a bore of a different length or shape. More particularly, adaptor 26 is designed to only seat within the bore of an endo head 16, and not within the bore of standard size heads (FIGS. 5–7). Since the bore length and shape for each endo head is identical, the adaptor according to the present invention is designed to fit within any endo head bore. The assemblies shown in FIGS. 2–4 illustrate an adaptor 26 that is securely and properly seated within head bore 24 of endo heads 16 and 16'. In particular, outer surface 38 of protruding portion 30 frictionally engages inner seating surface 22 of bore 24 sufficiently to securely seat adaptor 26 within bore 24. Adaptor 26 is properly seated and frictionally retained within bore 24 of endo head 16 because the bore length is sufficient to receive protruding portion 30, including reduced portion 42. In addition, the Morse-type taper of both outer surface 38 and inner seating surface 22 permits a secure frictional fit therebetween. In order to provide visual confirmation that adaptor 26 is properly seated, a slight visible gap 52 (about 0.020 inch) is formed between flat surface 20 of head 16 and inner face 32 of rim 28.

FIG. 3 illustrates an endo head 16' of a different size, but with a bore 24' that accommodates adaptor 26.

Referring now to FIGS. 5–7, there are shown a plurality of standard size heads having varying neck lengths. As noted earlier, the head diameter of the standard size femoral heads for total hip replacement prostheses are smaller than that of the endo heads. For example, the sizes of the standard femoral heads commercially available from Zimmer, Inc. range from a head diameter of 22 mm to a head diameter of 32 mm. Referring in particular to FIG. 5, there is shown a standard femoral head 54 having a short neck length, wherein head 54 includes a bore 56 therein having a tapered inner wall surface 58 and a straight cylindrical portion with a tent-shaped inner end surface 60. Adaptor 26, which is inserted in bore 56, is not able to be properly seated and frictionally retained therein because bore 56 is of an inappropriate length to properly receive protruding portion 30. In particular, bore 56 is too long, such that inner face 32 of rim 28 engages flat bottom surface 66 of head 54 to prevent any further axial reception of protruding portion 30. As a result, the bore inner wall surface 58 and the taper of outer surface 38 of protruding portion 3 do not frictionally engage, thus resulting in gap 62 being formed. Additionally, visual confirmation of the improper seating is provided by there being no gap or an actual contact surface 64 between inner face 32 of rim 28 and flat bottom surface 66 of head 54.

FIGS. 6 depicts a standard femoral head 68 having a medium neck length, wherein head 68 includes a bore 70 therein having a tapered inner wall surface 72 and a straight cylindrical portion with a tent-shaped inner end surface 74. Adaptor 26, which is inserted in bore 70, is not able to be properly seated and frictionally retained therein, since bore 70 is of an insufficient length to receive substantially all of protruding portion 30. In particular, top surface 44 of the raised boss engages end surface 74 to prevent any further axial reception of protruding portion 30. As a result, inner wall surface 72 does not frictionally engage outer surface 38 of protruding portion 30, resulting in a gap 76 being formed. Visual confirmation of the improper seating is shown by a large gap 78 formed between inner face 32 of rim 28 and bottom surface 80 of head 68.

Referring now to FIG. 7, there is shown a standard femoral head 82 having a long neck length, wherein head 82 includes a bore 84 therein having a tapered inner wall surface 86 and a straight cylindrical portion with a tent-shaped inner end surface 88. Again, for the same reasons as described above for head 68, adaptor 26, which is inserted in bore 84, is not able to be properly seated and frictionally retained therein. Since bore 84 is of an insufficient length to receive substantially all of protruding portion 30, a gap 90 is formed between inner wall surface 86 and outer wall surface 38 of protruding portion 30. Again, visual confirmation of the improper seating is shown by large gap 92 formed between inner face 32 of rim 28 and bottom surface 94 of head 82.

The standard femoral heads depicted in FIGS. 6–7 each has a bore whose length is too short to permit adaptor 26 to properly seat therein, while the standard femoral head depicted in FIG. 5 has a bore whose length is too long. Alternatively, adaptor 26 may be configured to properly seat within only those bores having a particular shape that is not specifically related to bore length. For example, the raised boss portion of adaptor 26 may be configured to be received by only those bores having an inner end that is shaped to properly seat and frictionally retain the raised boss portion therein. In this example, other shapes of a similar length would be insufficient to retain the raised boss portion therein.

It will be appreciated that the foregoing is presented by way of illustration only, and not by way of any limitation, and that various alternatives and modifications may be made to the illustrated embodiment without departing from the spirit and scope of the invention.

What is claimed is:

1. A set of hip prosthesis components including a plurality of head components and an adaptor component for use in assembling together one of said head components and a femoral stem component, wherein one of said head components is selected for engagement with said adaptor component, each of said head components including a bore and said adaptor component including an axially extending protruding portion that is configured for engagement with the bore of a selected head component, wherein a first head component includes a first bore that is of a first axial length and a second head component includes a second bore that is of a second axial length, said adaptor being configured to securely seat within only said first head component, wherein said first axial length of said first bore is sufficient for said first bore to accept and frictionally retain therein said protruding portion, and wherein said second axial length of said second bore is insufficient or inappropriate for said second bore to frictionally retain therein said protruding portion, and wherein said adaptor component includes at its outer axial end a rim portion that extends radially outwardly of said protruding portion, and wherein said second axial length of said second bore is either too short or too long, such that when said second axial length is too long, said rim portion engages a bottom surface of said second head component to prevent any further axial reception of the protruding portion into the second bore, thereby preventing the adaptor component from being frictionally retained in the second bore; and wherein when said second axial length is too short, a top surface of the adaptor component engages an inner end surface of the second bore to prevent all of the protruding portion of the adaptor component from being received in the second bore, thereby preventing the adaptor component from being frictionally retained in the second bore.

2. The set of hip prosthesis components of claim 1, wherein said first bore includes a tapered inner seating surface and said protruding portion includes a tapered outer surface for frictional engagement with said inner seating surface, the taper of said inner seating surface being substantially identical to the taper of said outer surface.

3. The set of hip prosthesis components of claim 2, wherein the taper of said inner seating surface and the taper of said outer surface are each a Morse taper.

4. The set of hip prosthesis components of claim 1, wherein said first head component includes a generally flat bottom surface and said rim portion includes a generally flat inner surface, wherein said bottom surface and said inner surface are spaced a slight distance from one another while said adaptor component is securely seated within said first head component, said distance being such to provide visual confirmation that said adaptor component is properly seated within said first head component.

5. The set of hip prosthesis components of claim 1, wherein said protruding portion of said adaptor comprises an outer frusto-conical surface and an inner frusto-conical surface, wherein said outer surface is receivable and frictionally retainable within a bore of said first head component, and is receivable, but not frictionally retainable within a bore of said second head component, and wherein a neck portion of said femoral stem component is receivable within said inner surface.

6. The set of hip prosthesis components of claim 5, wherein said protruding portion includes at its inner end a reduced diameter portion generally comprising a raised boss.

7. The set of hip prosthesis components of claim 1, wherein said first head component has a spherical diameter of at least 38 mm, and said second head component has a spherical diameter less than 38 mm.

* * * * *